United States Patent [19]

Steer

[11] Patent Number: 4,931,045
[45] Date of Patent: Jun. 5, 1990

[54] LOW PROFILE OSTOMY BAG COUPLING

[75] Inventor: Peter L. Steer, Surrey, England

[73] Assignee: E. R. Squibb and Sons, Inc., Princeton, N.J.

[21] Appl. No.: 215,171

[22] PCT Filed: Dec. 7, 1987

[86] PCT No.: PCT/GB87/00885

§ 371 Date: Jul. 5, 1988

§ 102(e) Date: Jul. 5, 1988

[87] PCT Pub. No.: WO88/04162

PCT Pub. Date: Jun. 16, 1988

[30] Foreign Application Priority Data

Dec. 9, 1986 [GB] United Kingdom ............... 8629424

[51] Int. Cl.$^5$ .............................................. A61F 5/44
[52] U.S. Cl. ................................................... 604/338
[58] Field of Search ............................ 215/345, 352; 604/332-345

[56] References Cited

U.S. PATENT DOCUMENTS

| | | | |
|---|---|---|---|
| 4,460,363 | 7/1984 | Steer et al. | 604/336 |
| 4,518,389 | 5/1985 | Steer et al. | 604/339 |
| 4,610,676 | 9/1986 | Schneider et al. | 604/339 |
| 4,610,677 | 9/1986 | Mohiuddin | 604/339 |

FOREIGN PATENT DOCUMENTS

| | | |
|---|---|---|
| 163979 | of 1985 | European Pat. Off. . |
| 2385386 | of 1978 | France . |
| 85/03427 | 8/1985 | PCT Int'l Appl. . |
| 1021145 | of 1966 | United Kingdom . |
| 1571657 | of 1980 | United Kingdom . |
| 1579875 | of 1980 | United Kingdom . |
| 2121902 | of 1984 | United Kingdom . |
| 2153683 | of 1985 | United Kingdom . |
| 2163350 | 2/1986 | United Kingdom . |
| 2173403 | 10/1986 | United Kingdom . |
| 2181652 | 4/1987 | United Kingdom . |
| 2183481 | 6/1987 | United Kingdom . |
| 2193097 | 2/1988 | United Kingdom . |
| 2193098 | 2/1988 | United Kingdom . |

Primary Examiner—Jerome L. Kruter
Attorney, Agent, or Firm—Donald J. Barrack; Robert E. Lee, Jr.

[57] ABSTRACT

A two-part ostomy coupling has a first part which is a flat annulus having inner and outer peripheral walls. With the annulus these walls define a shallow channel. The coupling has a second part formed by a second flat annulus with radially inner and outer rims formed by respective flexible peripheral elements of plastics material. The first and second parts are constructed so that the second part is a push fit into the shallow channel defined by the first part. An annular member having a flexible resilient strip extending inwardly from its radially inner edge and an element extending from its radially outer edge which can engage under a rim portion of the said outer peripheral wall. Alternatively, the second part may be an annular member having a flexible resilient strip extending outwardly from its radially outer edge and an element extending from its radially inner edge which can engage under a rim portion of the said inner peripheral wall.

5 Claims, 9 Drawing Sheets

LOW PROFILE OSTOMY BAG COUPLING

BACKGROUND OF THE INVENTION

This invention relates to a coupling for joining an ostomy bag to a pad or surgical dressing. Ostomy bags are usually secured to a pad or surgical dressing which contacts the user's skin and surrounds the stoma. The term 'ostomy bag' is intended to include colostomy, ileostomy, urostomy and other bags used for example after surgical intervention procedures. There is a need for a coupling between pad and bag which allows the bag to be readily removed when necessary, and replaced by a clean, empty bag, At the same time, it is essential that the coupling should be a secure one, and prevent leakage particularly of liquids and gases.

Efforts were made some time ago, see for example the proposal in British Patent Specification No. 1 021 145 published in 1966, to provide a connector whereby the bag can be readily removed and replaced. But this arrangement involves two separate operations, unscrewing and then removal. That is, first one must unscrew the connector which carries the bag from the connector which is secured to the body and this involves a risk of leakage as it is necessary to invert the bag. Also it is an awkward operation. It will be appreciated that at this time the bag is full or partly full of bodily waste products, and manipulation of the coupling will be an unpleasant operation even if, as is often not the case, the user has a high degree of dexterity.

British Patent Specification No. 1 099 455 discloses an appliance in which one ring co-operates with a second part-ring which is used to trap the neck of a bag when the two rings are inter-engaged with the bag mouth between them. If adequate security against leakage is to be provided, it is necessary that the two rings should be a tight fit; however, this makes it difficult for the user to pull off the part-ring. As th part-ring is pulled off, there is the probability that the security of attachment of the first ring to the surgical dressing, or of the dressing to the skin of the wearer, will be impaired. This may also cause discomfort to the wearer.

A more recent and commercially successful proposal is described and claimed in British Patent No. 1 571 657. While the ostomy bag coupling according to Patent No. 1 571 657 has enjoyed wide user acceptability, the search for a simpler coupling which at the same time is of flatter design has continued. It will be understood that a flatter design is desirable in order that the bag when worn under clothes should be unobtrusive.

An ostomy coupling is shown in U.K. Patent Application No. 2 153 683(J. V. Edwards). This adopts the known concept of a deflectible seal strip and relies on a single strip of plastics to serve a sealing function between two connected coupling rings; in addition the seal strip is involved in transmitting to the body side coupling substantially all of the downward forces arising from the weight of the bag and its contents. In this design, the load applied to the seal strip may well cause its effectiveness as a seal to deteriorate. This application also shows a rotatable ring for attachment of a belt. The present Applicant is unaware of any current commercial utilization of the device shown in the Edwards application.

SUMMARY OF THE INVENTION

According to one aspect of the present invention, a two part ostomy coupling has a first part in the form of a first flat annulus having inner and outer peripheral walls which with the annulus define a shallow channel, and a second part formed by a generally annular member having radially inner and outer rims formed by respective flexible peripheral element of plastics material, the parts being constructed and arranged so that the second part is a push fit into the shallow channel.

In a preferred form of the invention, the flexible peripheral elements are formed integrally with the remainder of the annular member and are shaped to taper radially outwardly. More preferably each of these tapering elements is tilted out of the plane of the remainder of the annular member. The radially outer wall of the first flat annulus is preferably provided with a radially inwardly directed projection at or near its rim remote from the flat annulus. This arrangement of the projection and the elements allows the element to be "sprung" past the projection when the two parts of the coupling are assembled together. This assembly may be done by a simple manual pressing together.

The radially inner wall defining the shallow channel is preferably angled slightly radially inwardly over a part of its height. The purpose of this is to give a lead-in guide and facilitate the manual fitting together of the first and second coupling parts.

According to another aspect of the invention, there is provided an ostomy coupling including a first part and a second part, the first part being in the form of a flat annulus having inner and outer peripheral walls which with the annulus define a shallow channel for reception of the second part, the second part being an annular member having a flexible resilient strip extending inwardly from its radially inner edge and an element extending from its radially outer edge which can engage under a rim portion of the said outer peripheral wall.

According to a further aspect of the invention, there is provided an ostomy coupling including a first part and a second part, the first part being in the form of a flat annulus having inner and outer peripheral walls which with the annulus define a shallow channel for reception of the second part, the second part being an annular member having a flexible resilient strip extending outwardly from its radially outer edge and an element extending from its radially inner edge which can engage under a rim portion of the said inner peripheral wall.

In one advantageous form of the invention, the bag side coupling part may be constructed to include a filter housing, in accordance with the teaching of our co-pending European Published Application No. 210032.

The invention will be better understood from the following non-limiting description of examples thereof given with reference to the accompanying drawings in which:

DESCRIPTION OF THE PREFERRED EMBODIMENTS

The illustrated ostomy bag coupling comprises a first part 10 and a second part 20. In the preferred embodiment of the invention, the first coupling part 10 is the body-side coupling part and the second part 20 is the bag side coupling part. In an alternative embodiment of the invention, the first part 10 could be the bag side coupling part and the second part 20 could be the body-side coupling part. In that event, of course the ostomy bag would be secured to the first coupling part 10.

Referring now to FIGS. 1-4, the illustrated body-side coupling part 10 is preferably made by injection moulding from low density polyethylene. It may alternatively be moulded from E.V.A. or from a low density polyethylene with some added E.V.A. The coupling part 10 includes a flat annulus 11 having a radially inner wall 12 and a peripheral wall 13. It has a stomal aperture 14. In use it is attached to a pad of medical grade adhesive 15. Suitable adhesive materials for this purpose include, for example, those described by Chen in U.S. Pat. No. 3,339,546; by Chen et al. in U.S. Pat. No. 4,192,785; by Pawelchak et al. in U.S. Pat. No. 4,393,080; and by Doyle et al. in U.S. Pat. No. 4,551,490. A particularly suitable material is that sold under the Registered Trade Mark STOMAHESIVE by E. R. Squibb & Sons Limited of Hounslow, Middlesex. The pad 15 may be provided with a stomal aperture 15a or such an aperture may be cut in a complete pad by the user just prior to applying it to his or her peristomal area. The peripheral wall 13 has a continuous inwardly projecting projection 16 thereon, the extent of its projection radially inwardly being in the region 0.004-0.008 inches (0.1-0.2 mm).

Figure 1:
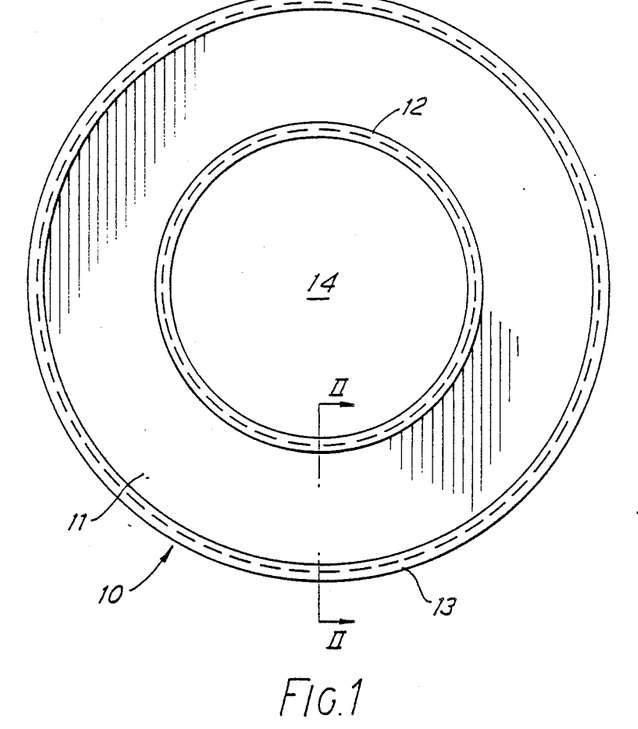
FIG. 1 is a front view of one example of a first coupling part useful in a coupling according to one embodiment of the present invention.
Figure 2:
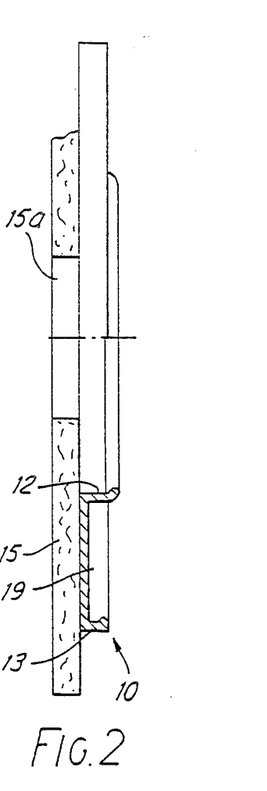
FIG. 2 is a cross-section on the plane II—II of part of the coupling part shown in FIG. 1 and also showing an adhesive pad.
Figures 3, 4, 7, 8:
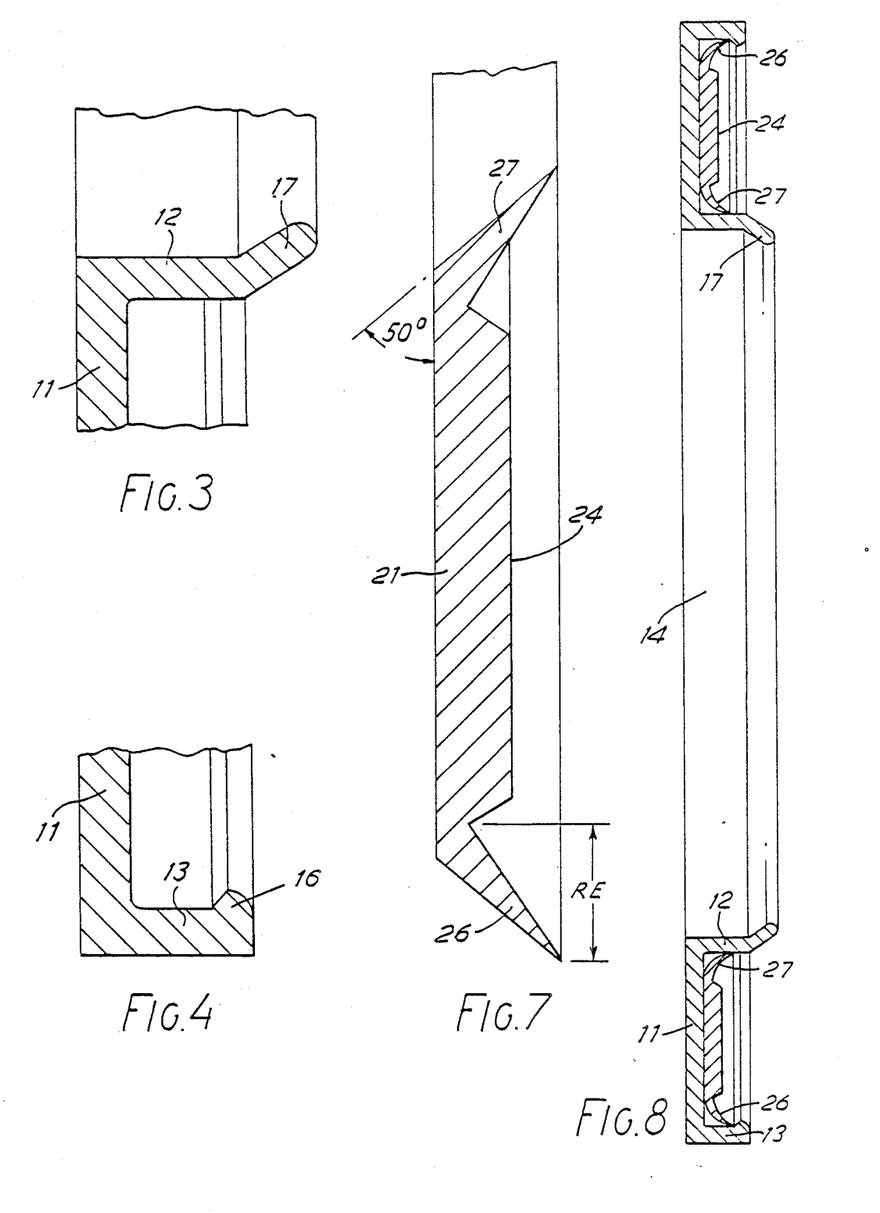
FIGS. 3 and 4 are views on a larger scale showing radially inner and outer walls which define a shallow channel.
FIG. 7 is an enlarged cross sectional view of a portion of the part shown in FIG. 6.
FIG. 8 illustrates the parts shown in FIGS. 1 and 5 in assembled condition.

The radially inner wall 12 has a portion 17 remote from the annulus 11 which is angled radially inwardly as best seen in FIG. 3. For example, it may be angled radially inward at an angle of between 25°-60° to the remainder of the wall 12. This angled portion 17 provides a lead-in guide when the bag side coupling part is being coupled to the body side coupling part, an operation which is easily done with a gentle manual press fitting.

Figures 5, 6:
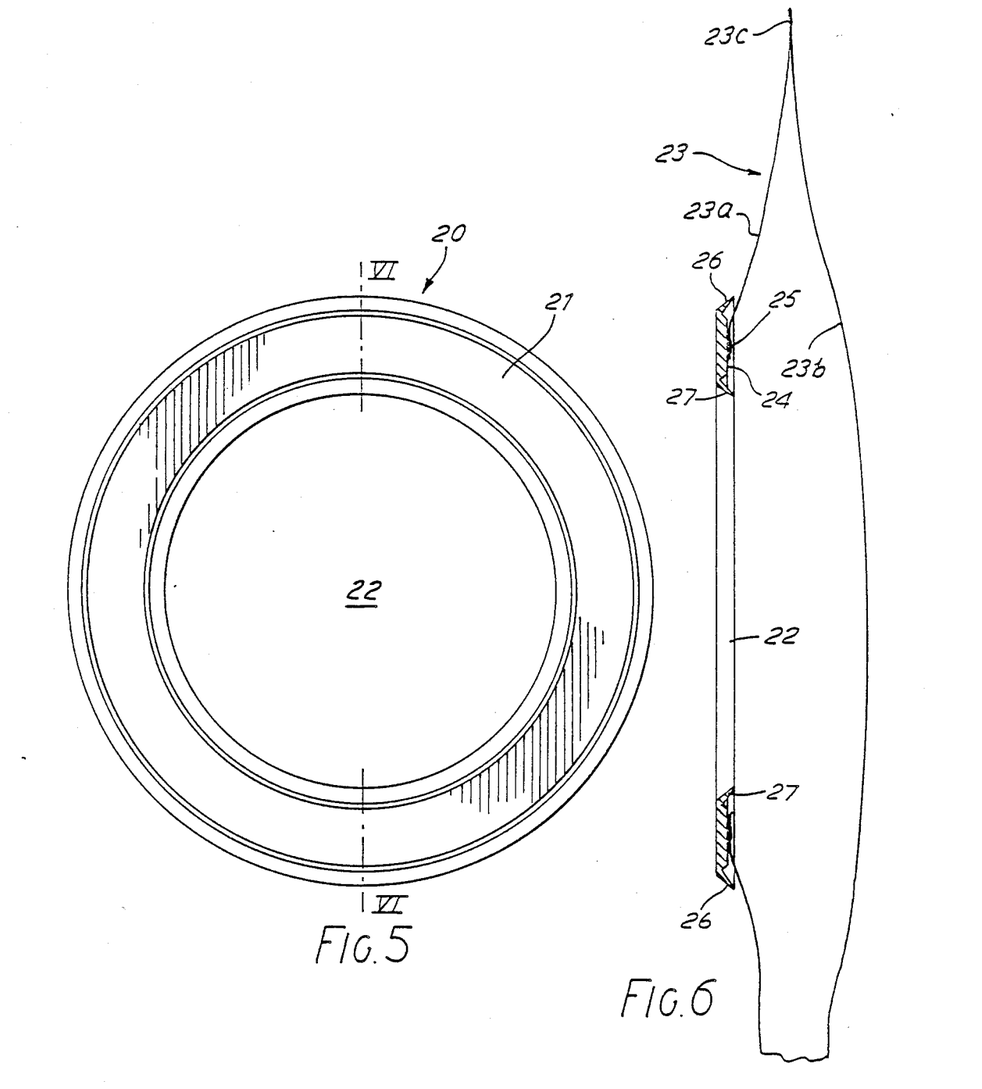
FIG. 5 is a front view of a second coupling part intended for use in a coupling according to the invention.
FIG. 6 is a cross sectional view on the plane VI—VI of FIG. 5.

Referring to FIGS. 5-7, the illustrated bag side coupling part 20 is preferably made from the synthetic plastics material known as E.V.A. For example one may employ E.V.A. Grade UL 00209 sold by Esso Chemicals. The coupling part 20 includes a flat annulus 21 having a stomal aperture 22. An ostomy bag 23 is attached to one surface 24 of the flat annulus for example by a weld seam 25. The bag side coupling part 20 has radially inner and outer rims formed by respective flexible peripheral elements 26 and 27. As seen best in FIG. 7, these flexible elements are angled to the plane of the annulus 21, for example at an angle between 40° and 60°, preferably 50° to the said plane. Moreover, the flexible elements taper in a direction away from the remainder of the annulus. Preferably, the whole part 20 is integral and made by injection moulding. As illustrated, the tips of the flexible elements 26 and 27 stand proud of the surface 24 of the body side coupling part 20 by a distance which is from about 40-70% of the thickness of the annulus 21. However, this particular ratio is not essential to the invention.

The ostomy bag 23 as seen in FIG. 6 has bag walls 23a, 23b, joined by a peripheral weld seam 23c and the wall 23a has a stomal aperture therein, and surrounding that aperture there is the weld seam 25 which connects the bag wall 23a to the annulus 21.

In operation, due to the flexibility of the elements 26 and 27, removal of a bag from a body side coupling element while it is still on the body can readily be done by holding with one hand the peripheral wall 13 on the body side coupling part and, with the other hand, pulling at one peripheral location by grasping the bag wall adjacent to that location and pulling it directly away from the body. The flexible elements 26 and 27 then spring out from the shallow channel 19 at that peripheral location and the remainder of the bag side coupling part can then be peeled off without difficulty.

In fitting a clean bag onto the body side coupling part, the stoma aperture 22 of the bag side coupling part is approximately aligned with the stomal aperture 14 and the radially inner rim of the annulus 21 defined by the flexible flange 27 is guided by the wall portion 17 so that the bag side coupling part becomes fully aligned with the body side coupling part. Thereafter, gentle pressure suffices to connect these two parts and in the connected condition, the radially outer flange 26 engages under the projection 16 on the wall 13.

As will be understood, for best results, it is desirable for there to be a carefully chosen relationship between the inner and outer diameters of the extremities of the bag side coupling part 21 and the inner and outer boundaries of the shallow channel 19. In one particulary preferred embodiment of the invention, the following dimensions have proved to be a satisfactory compromise between the conflicting requirements of good sealing, security of attachment, and ease of connection and removal.

TABLE I

| | |
|---|---|
| Overall diameter (tip-to-tip) of part 20 (herein called OD 20): | 2.421 ins. (61.5 mm) |
| Diameter of stomal aperture 22 (tip-to-tip) (herein called DSA): | 1.621 ins. (41.2 mm) |
| Inside diameter of wall 13: | from 98.8 to 99.9% of OD20 |
| Outside diameter of wall 12: | from 98.2 to 99.8% of DSA |
| Radial extent of flexible elements 26,27 | from 2.2 to |

TABLE I-continued

| | |
|---|---|
| (distance RE in FIG. 7): | 2.3% of OD20. |

Of course it will be appreciated that the present invention is not limited to the use of these particular dimensions. Different dimensions may be preferable if different plastics materials are employed.

By employing a shallow channel and flexible elements on the radially inner and outer rims of a substantially flat annulus, an effective ostomy coupling can be obtained which is at the same time easy to fit and remove and of such a flat construction that it meets all reasonable requirements for unobtrusiveness when worn.

Figure 9:
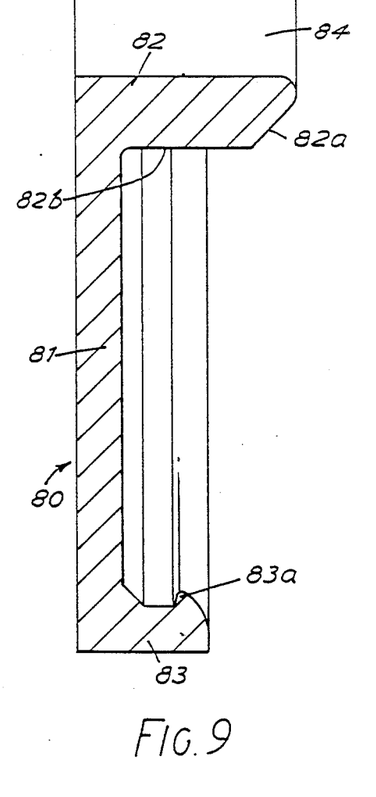
FIG. 9 illustrates in radial cross-section a second embodiment of a body side coupling part, made generally in the form of a shallow channel, in accordance with the invention.
Figure 9A:
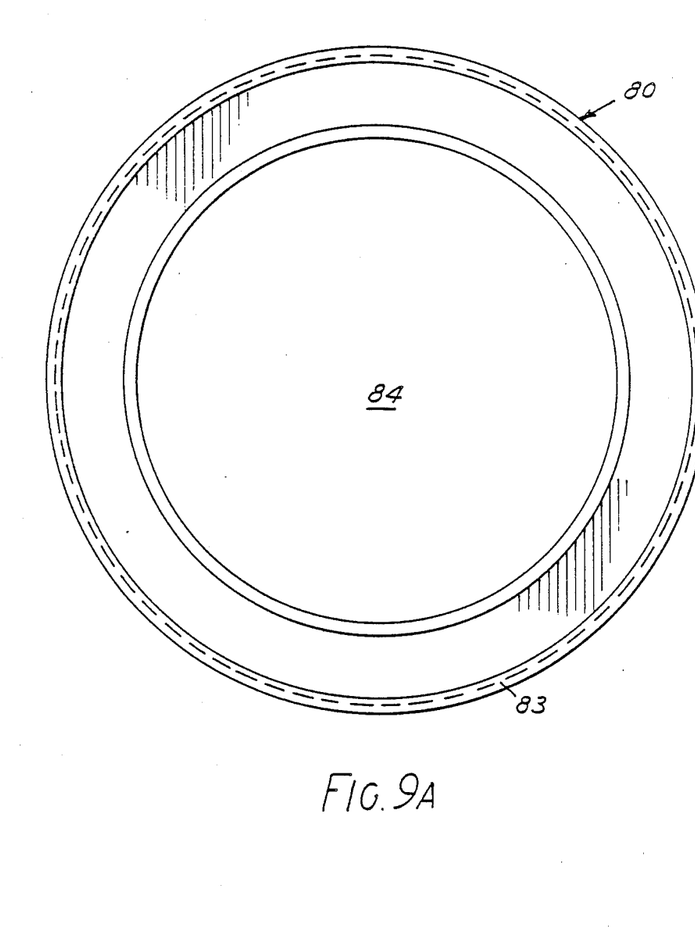
FIGS. 9A and 9B are elevation and part-sectional views thereof.
Figure 9B:
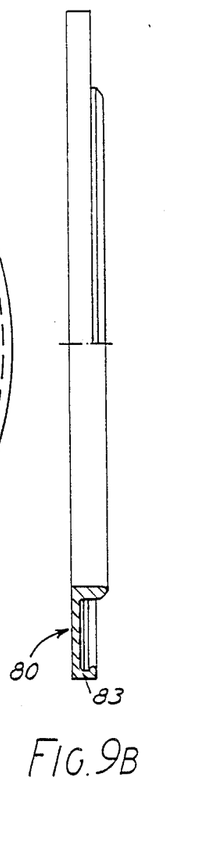
Figure 10:
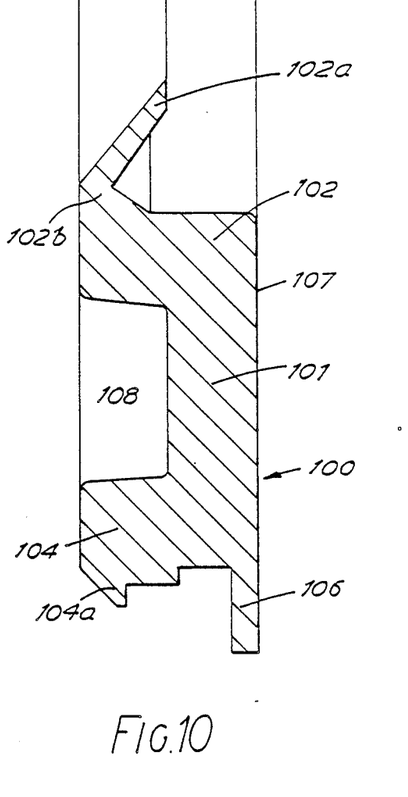
FIG. 10 illustrates a second embodiment of a bag side coupling part, intended for co-operation with the body side coupling part of FIG. 9.
Figure 11:
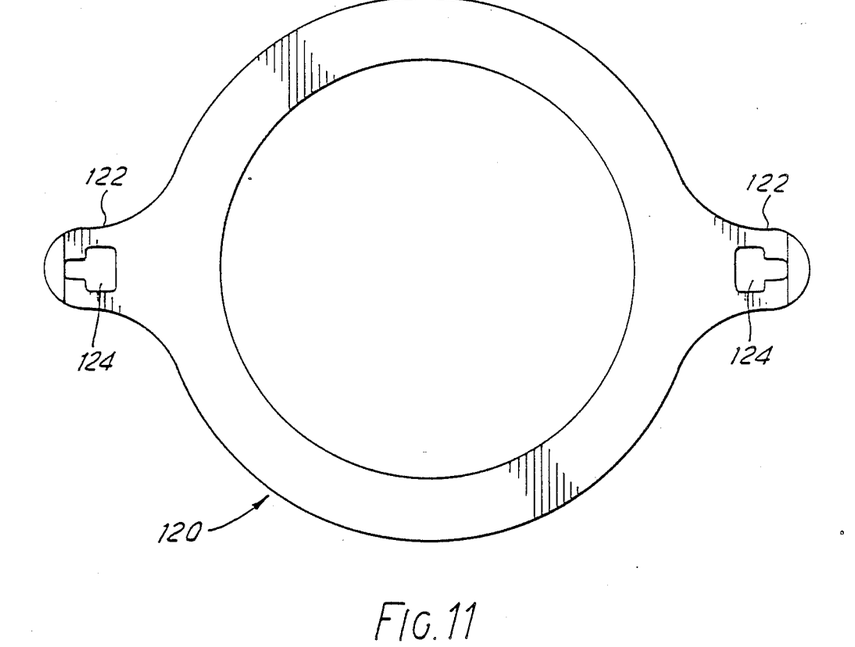
FIGS. 11 and 11A illustrate one example of an optional belt retaining ring.

A second embodiment of the invention will now be described. FIG. 9 illustrates a body side coupling part 80, intended to co-operate with a bag side coupling part 100 which is shown in FIG. 10. Optionally used with these parts is a bag retaining ring 120 which is shown in FIG. 11. These parts 80, 100, 120 are shown in their assembled condition in FIG. 12. FIGS. 9A and 9B are, on a smaller scale, respectively elevation view and half axial cross section of the body side coupling part shown in FIG. 9.

Referring now to FIGS. 9–12, the illustrated embodiment of an ostomy coupling is readily coupled and uncoupled by the use of minimum force and a peeling action, and has the advantage of a low overall height (outstand from the body of the wearer). The body side part 80 may be made by injection moulding of low density polyethylene, and in use is attached to a pad of medical grade adhesive (not shown in FIGS. 9–12) in a similar way as is shown in the embodiment of FIGS. 1–4. The body side part 80 includes a substantially flat annulus 81 having a radially inner wall 82 upon which is a lead-in slope or chamfer 82a, and a radially outer wall 83. The stomal aperture is indicated at 84. The wall 83 has an inturned rim portion 83a. As it is desirable for ostomy couplings to be unobtrusive when worn under clothing, the height (i.e. axial length) of the wall 82 is preferably about 0.125" (3.2 mm) approx and that of the wall 83 is preferably about 0.075" (1.9 mm) approx.

The bag side part 100 may be made of E.V.A. synthetic plastics and includes an annular portion 101, a radially inner wall portion 102 having a resilient flexible encircling strip 102a at its inner periphery and a radially outer engagement portion 104. The latter has a radially outwardly extending lip or rim 104a which, when the two coupling parts are connected, hooks under the inturned rim portion 83a of the body side coupling part 80. The rim portion 83a is preferably relatively rigid.

It is not essential, though it is preferred, that the rim 83a extends around the whole periphery of the engagement portion 104; in alternative embodiments of the invention a series of peripherally-spaced lips could be used instead of the continuous rim 83a. In other words, a castellated rim could be employed. This could be of use when it is desired to have the parts 80 and 100 separable by application of a slight force.

The radially outer part of the engagement portion 104 has a stepped configuration providing a channel 105 for receiving the radially inner edge 121 of the belt retaining ring 120. The portion 101 also has a flange portion 106. The bag is attached in a conventional way to the annular surface 107.

The annular bag side coupling part 100 is seen in its undeformed condition in FIG. 10 and in this condition the encircling flexible strip 102a extends at about 50 degrees (other angles may be suitable) to the axis of rotation of the coupling part 100. When assembled into the channel-shaped part 80, as can be done with light manual pressure, this strip 102a is bent towards the adjacent portion 102.

Figure 12:
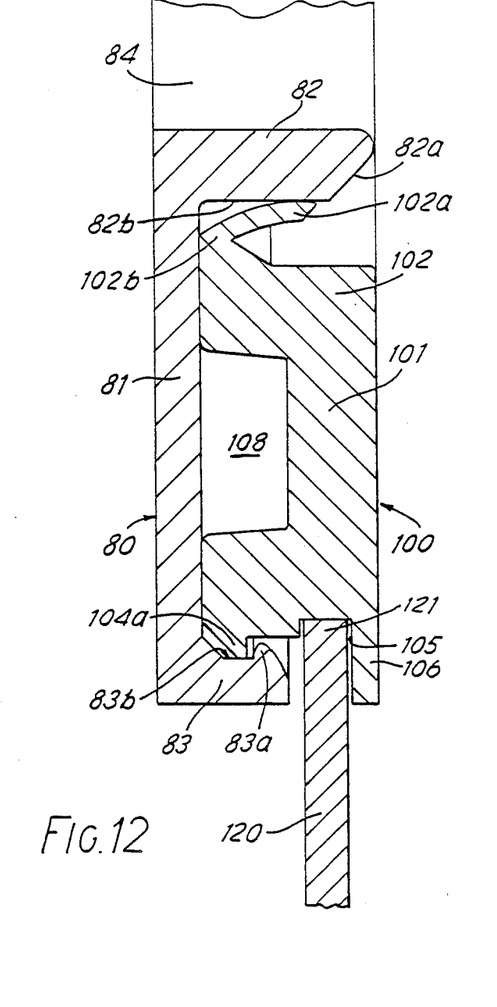
FIG. 12 illustrates these parts in mutually coupled condition.

As seen in FIG. 12, the parts 80 and 100 in their assembled positions are coupled together due to the interengagement at 83a, 104a and the strip 102a is flexed inwardly from its normal undeformed postion. Due to its resilience, it presses against the outer surface 82b of the wall 82. This tends to urge the lip or rim 104a under the interned rim 83a and so increases the security of attachment between the two coupling parts 80 and 100. It also improves the fluid seal between these two parts.

The ring 120 is connected to a belt or truss in conventional manner and aids in holding the appliance in the correct position on the wearer's body.

In its undeformed condition the strip 102a may extend substantially linearly from the adjacent root portion 102b of the wall portion 102, at an angle (from about 20°–60° would be suitable) to the axis of rotational symmetry of the part 100. Alternatively, it may extend arcuately from the root portion 102b, but in either event it is desirable that the distance measured transverse to the axis between the radially innermost part of the strip 102a and the radially outermost part of the rim 104a should be from 100.2% to 103% of the distance between the surfaces 82b and 83b (FIG. 9) of the walls 82, 83. The invention is not limited to these particular values; other values may be employed, e.g. if different plastics materials are used.

As illustrated, the part 100 contains a substantial recess 108 of annular channel shape. This is optional and could be dispensed with by making the part 100 largely a solid annulus, but it is included in the interest of saving material.

Figure 11A:
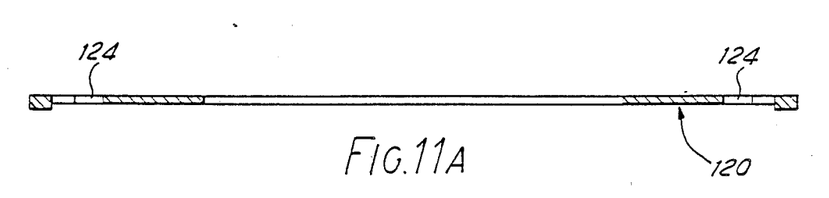

The belt retaining ring need not be used in cases where the security of attachment of the medical grade adhesive pad to the wearer is adequate. As an alternative to a belt retaining ring, apertured lugs (similar in design and position to lugs 122 of FIG. 11) may be provided on or formed integrally with either the body side or bag side coupling part. Referring now to FIG. 11, the illustrated belt retainer ring 120 has lugs 122 through the apertures 124 of which one threads or clips a suitable belt or harness, in conventional manner. FIG. 11A is a central cross-section through the ring 120.

A third embodiment of the invention is illustrated in FIGS. 13–16.

Figure 13:
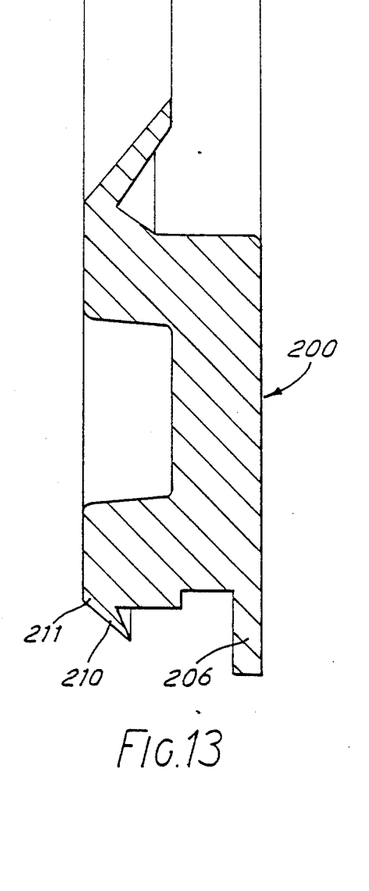
FIG. 13 illustrates in radial cross-section a third embodiment of bag side coupling part, intended for use with the body side part of FIG. 9.
Figures 14, 15:
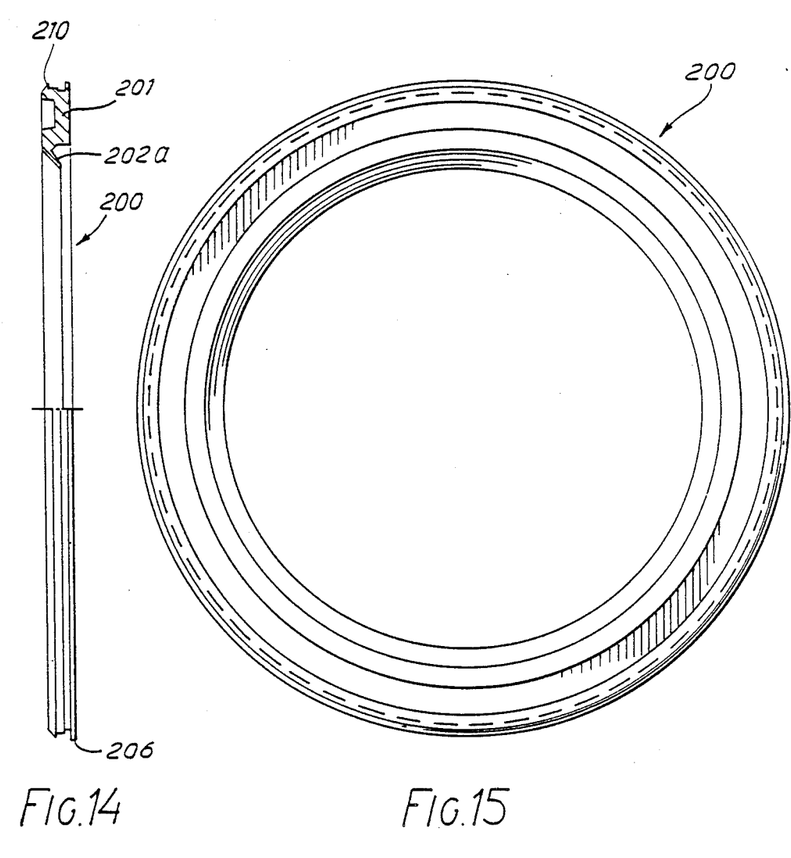
FIGS. 14 and 15 are respectively part section and elevation views of the parts shown in FIG. 13.
Figure 16:
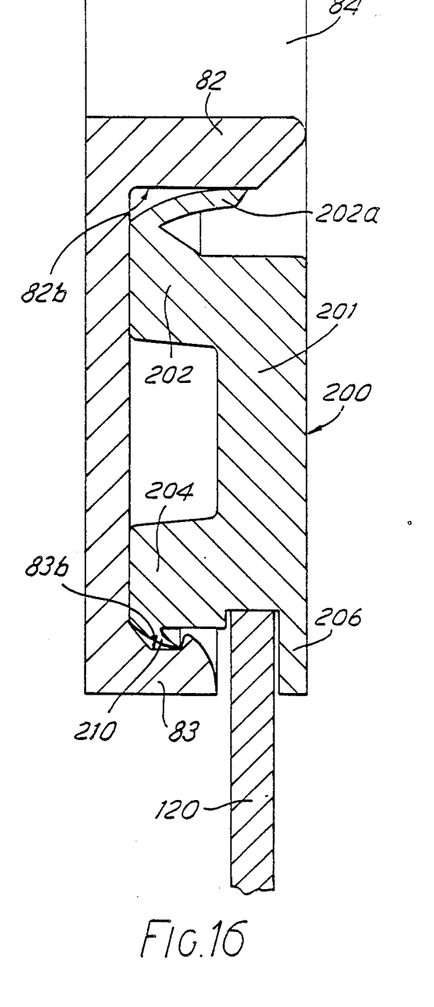
FIG. 16 shows these parts in mutually coupled condition, i.e. as on a wearer in normal use.

The embodiment of the invention illustrated in FIGS. 13–16 is similar to that of FIG. 10. FIGS. 14 and 15 are respectively part-section and elevation views, and in FIGS. 13–16 the reference numerals used for like parts to those seen in FIG. 10 are similar numerals but with 100 added. In the FIG. 13–16 embodiment, the bag side coupling part 200 has a flexible peripheral seal strip 210 instead of the rim 104a. The seal strip 210 peripherally encircles the member 200 and tapers in a direction away from its root end 211 where it is connected to the remainder of the part 200. The strip 210 is preferably moulded integrally with the rest of the part 200 but may alternatively be separately attached e.g. by adhesive. The coupling part 200 co-operates with a body side coupling part 80. This embodiment of the invention retains the low profile advantage of the FIG. 10 embodiment and has the further advantage that the liquid sealing between the parts 80 and 200 is enhanced by the presence of the seal strip 210. It is preferred that the overall dimension in the direction normal to the axis of rotational symmetry between the radially innermost part of strip 102a and the radially outermost part of strip 110 should be from 100.5% to 104% of the distance between the surfaces 82b, 83b of the walls 82, 83. These proportions, however, are not crucial to the invention.

The use of an ostomy appliance embodying bag side coupling parts as illustrated in FIGS. 10 and 13 is essentially the same as that described in connection with FIGS. 1-8.

What is claimed is:

1. A two part ostomy coupling having a first part in the form of a first flat annulus having inner and outer peripheral walls which with the annulus define a shallow channel, and a second part in the form of a second flat annulus having radially inner and outer rims formed by respective flexible peripheral elements of plastics material, the parts being constructed and arranged so that the second part is a parallel push contiguous fit into the shallow channel, said flexible peripheral elements being angled out of the plane of the remainder of the second flat annulus.

2. A coupling according to claim 1 in which the flexible peripheral elements are formed integrally with the remainder of the second flat annulus and are shaped to taper radially outwardly.

3. A coupling according to claim 1 in which the peripherally outer wall of the first flat annulus is provided with a radially inwardly directed projection at or near its rim remote from the flat annulus.

4. A coupling according to any of claim 3 in which the peripherally inner wall defining the shallow channel is angled slightly radially inwardly over a part of its height, so that in use it serves to give a lead-in guide and facilitate the manual fitting together of the first and second coupling parts.

5. An ostomy coupling system according to claim 1 in which said first part comprises the body side coupling part of the ostomy appliance and includes a pad of medical grade adhesive, said first flat annulus secured to a surface of said adhesive pad and said second part comprises the bag side coupling part of the ostomy appliance and includes a bag secured to said second flat annulus.

* * * * *